US00PP37028P2

(12) United States Plant Patent
Kamimura

(10) Patent No.: US PP37,028 P2
(45) Date of Patent: Oct. 14, 2025

(54) ***ZOYSIA* GRASS PLANT NAMED 'NARUO1920'**

(50) Latin Name: ***Zoysia matrella* (L.) Merr.**
Varietal Denomination: NARUO1920

(71) Applicant: NARUO GOLF CLUB, Hyogo (JP)

(72) Inventor: Masatomo Kamimura, Hyogo (JP)

(73) Assignee: NARUO GOLF CLUB, Hyogo (JP)

( * ) Notice: Subject to any disclaimer, the term of this patent is extended or adjusted under 35 U.S.C. 154(b) by 0 days.

(21) Appl. No.: 18/765,675

(22) Filed: Jul. 8, 2024

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./390
CPC ..... A01H 5/12
See application file for complete search history.

(56) References Cited

U.S. PATENT DOCUMENTS

PP35,819 P2 * 5/2024 Akashi ..... A01H 6/469
Plt./390

* cited by examiner

*Primary Examiner* — Kent L Bell
(74) *Attorney, Agent, or Firm* — Oblon, McClelland, Maier & Neustadt, L.L.P.

(57) ABSTRACT

'NARUO1920' is a new plant of perennial *Zoysia* grass plant which is distinguishable from other *Zoysia* plants know to the Inventor by having a very short leaf length, fine leaves, and high creeping ability.

8 Drawing Sheets

Latin name of genus and species of plant claimed & variety denomation:

(1) Latin name (genus/species) of the plant claimed: *Zoysia matrella* (L.) Merr.

(2) Variety denomination of the plant claimed: 'NARUO1920'.

The present invention relates to a new and distinct asexually reproduced variety of perennial *Zoysia* grass plant (*Zoysia matrella* (L.)) Merr.

BACKGROUND OF THE INVENTION

In 1985, domestically produced *Zoysia* grass plant was introduced for use on greens in golf courses. The inventor subsequently discovered on a green geographically located at the Naruo Gold Club in Kawanishi, Hyogo, Japan that a putting green into which *Zoysia* grass plant had been introduced contained a rare plant of *Zoysia* grass plant characterized by fine and soft blades and a high shoot density. This new variety of plant. was named 'NARUO1920'.

The inventor subsequently isolated and cultivated the new plant and conducted tests on it including assessments of phenotypes and plant stability. The inventor found that the new variety was not identified elsewhere in Japan. The inventor's characterization of the new plant showed that while its above-ground traits were small in size that the growth was as vigorous as that of conventional 'Meyer' (not patented) and 'Emerald' (not patented) varieties. *Zoysia* grass plant varietal denomination 'TM9' also mentioned herein is described by U.S. Plant Pat. No. 17,514-P3 and US-20050114973-P1. *Zoysia* plants 'Meyer' (not patented) and 'Emerald' (not patented) have not been patented.

BRIEF SUMMARY OF THE INVENTION

'NARUO1920' was discovered growing on and isolated from a putting green geographically located in Kawanishi, Hyogo, Japan at Latitude: N34°53'39.9", Longitude: E135°23'53.9" in January 2016. Only a plant individual showing a dense phenotype with low grass height was isolated from the putting green. 'NARUO1920' was observed to have a phenotype that distinguished it from other *Zoysia* varieties growing on other putting greens. 'NARUO1920' was asexually reproduced and reproduces true to type.

Vegetative propagation comprising rhizomes and stolons was carried out and stability was confirmed. As a result of the basic characterization, it was confirmed that 'NARUO1920' was a new variety that had never existed before.

The inventor isolated this cultivar and carefully evaluated its phenotypes and stability. Amongst its other distinguishing phenotypes, compared to other *Zoysia* grass varieties, 'NARUO1920' has very fine blades, a higher density of creeping stems providing it with excellent creeping stem growth desirable on a putting green. These traits are uncommon in small turf which is known as Kourai grass. The new plant described herein provides excellent cover as characterized by lateral spread of the stolon despite the small size of this above ground part.

BRIEF DESCRIPTION OF THE DRAWINGS

This application contains at least one drawing executed in color.

FIGS. 4A-4B. Green Index (NDVI) on the turf of the test lines in Winter (February in Japan).

FIG. 4A compares the greenness of the experimental plots from May 2022 through May 2023 according to the Green Index (NDVI).

FIG. 4B shows the increased greenness of the 'NARUO1920' plot compared to the plots of 'TM9', 'Meyer', and 'Emerald' plants.

FIGS. 5A and 5B. Initial growth and covered rate in cultivars.

FIG. 5A shows initial growth in June, July and August for 'NARUO1920', 'TM9', 'Meyer', and 'Emerald' plants.

FIG. 5B, panels 1, 2, 3 and 4, respectively, show coverage of experimental plots on June 2021, October 2021, May 2022, and May 2023.

FIG. 6A compares leaf length (mm) of 'NARUO1920' to varieties 'TM9', 'Meyer' and 'Emerald'.

FIG. 6B compares stem length (mm) of 'NARUO1920' to varieties 'TM9', 'Meyer' and 'Emerald'.

FIG. 6C compares numbers of ears in Fall (Japan) of 'NARUO1920' to varieties 'TM9', 'Meyer' and 'Emerald'.

FIG. 6D compares stolon density (cm) of 'NARUO1920' to varieties 'TM9', 'Meyer' and 'Emerald'.

DETAILED BOTANICAL DESCRIPTION OF THE VARIETY

'NARUO1920' has very fine leaves and several shoots compared to common *Zoysia* grass. 'NARUO1920' had the lowest values of above-ground traits (leaf length and budding stem length) compared to standard cultivars, while it had the highest density of creeping stems. This indicates that 'NARUO1920' is a compact plant with excellent creeping stem growth. Height: 3.2 cm for 'NARUO1920', 5.8 cm for 'TM9', 9.6 cm for 'Meyer', and 4.8 cm for Emerald.

Spread (defined as the length of stolon per unit area): 344 $cm^2$ for 'NARUO1920', 288 $cm^2$ for 'TM9', 125 $cm^2$ for 'Meyer' and 175 $cm^2$ for 'Emerald'. Spread measured per 100 square centimeters.

Stolon Length of leaf sheath are, respectively, 6.9 mm/'NARUO1920', 6.7 mm/'TM9', 12.0 mm/'Meyer', and 17.5 mm/'Emerald'.

Density of hair on leaf sheath are, respectively, Sparse/'NARUO1920', Sparse/'TM9', Sparse/'Meyer', and Sparse/'Emerald'.

Internode lengths are respectively, 12.3 mm/'NARUO1920', 11.0 mm/'TM9', 18.6 mm/'Meyer', and 21.1 mm/'Emerald'.

Width of internodes are respectively, 0.9 mm/'NARUO1920', 1.1 mm/'TM9', 1.5 mm/'Meyer', and 1.1 mm/'Emerald'.

Figure 1A:
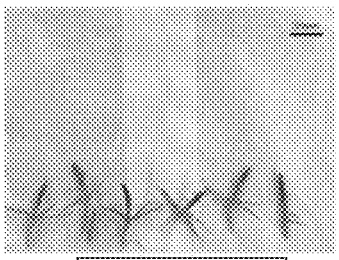
FIGS. 1A-1C. Spike stems of 'NARUO1920' and standard cultivars 'Meyer' and Emerald.
Figure 1B:
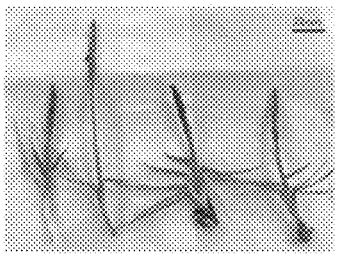
Figure 1C:
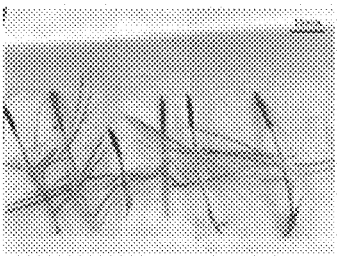
Figure 2A:
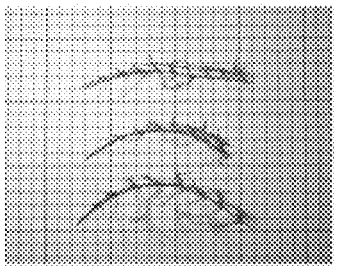
FIGS. 2A-2C. Stolons of 'NARUO1920' and standard cultivars 'Meyer' and 'Emerald'.
Figure 2B:
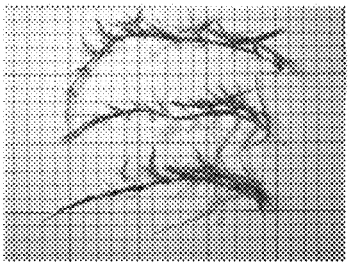
Figure 2C:
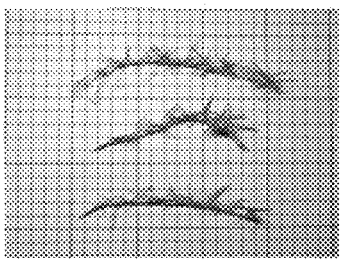

Stolon colors are respectively, 60B/'NARUO1920', 60A/'TM9', 60A/'Meyer', and 60A/'Emerald'; wherein the color codes are given by The R.H.S. Color Chart FIGS. 1A-1C show the number of ears in the initial stage of each test lines. The number of ears produced was higher than that of standard varieties 'Meyer' and 'Emerald', but the length of the stems produced was very short, FIGS. 1A-1C, FIGS. 2A-2C show the initial growth and cover of each tested lines.

Figure 3A:
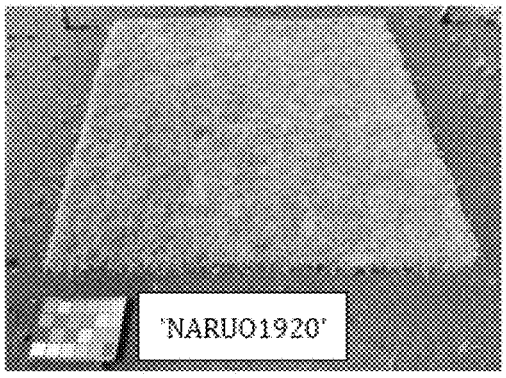
FIGS. 3A-3C. Turf of 'NARUO1920' and standard cultivars 'Meyer' and 'Emerald'.
Figure 3B:
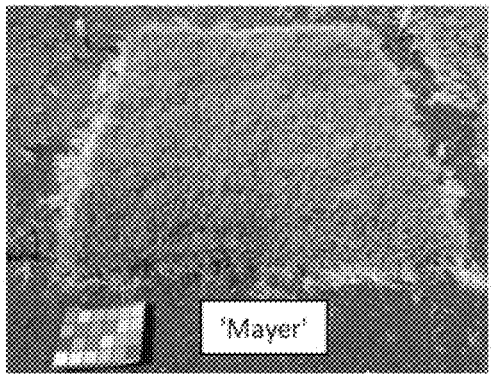
Figure 3C:
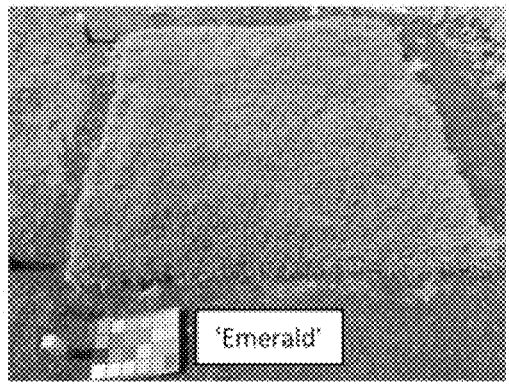

Although the above-ground portion of 'NARUO1920' is small, the growth of the filling stems is vigorous. The initial growth and cover speed of 'NARUO1920' are similar to standard varieties, although the above-ground portion was smaller. This is due to the high shoot density. This can be attributed to the large number of stolon densities as shown by FIGS. 3A, 3B and 3C.

Normalized Difference Vegetation Index (NDVI) was measured over time in the densely planted plots of the test cultivars and the trend of turfgrass color was compared.

The results showed that 'NARUO1920' exhibited a similar color trend to the standard varieties, but the color of 'NARUO1920' was most deep in February, the coldest month of the year in Japan. This indicates that 'NARUO1920' has higher color retention performance in winter than the other varieties.

'Meyer' is a variety of *Zoysia* (*Zoysia japonica*). Since 'Meyer' is a *Zoysia japonica*, it is generally the most dormant (withering in winter) variety. The results of this study also showed that 'Meyer' had the lowest NDVI value and the lowest color retention.

'Emerald' is not *Zoysia japonica*, but color retention was low in winter conditions compared to the standard variety.

Compared to the standard varieties 'NARUO1920' had very good color retention. Furthermore, the maintenance of greenness of 'NARUO1920' was visually confirmed as shown in FIG. 4B.

Description of other phenotypes of 'NARUO1920'. Growth characteristics of this plant are very strong creeping and very low erect stem length compared to 'Meyer' and 'Emerald'. The stem is slightly thicker than 'Emerald', approximately 1.0 mm to 1.5 mm in diameter. The creeping stems are reddish in color and the internodes are approximately 14.9 mm long. The reddish stolon color (Value/Variety) is described by The Royal Horticultural Society (R.H.S.) Color Chart is 60B for 'NARUO1920', 60A for 'TM9', 60A for 'Meyer', and 60A for 'Emerald'.

The length of the emerged ear is very short, approximately 8.5 mm, compared to the control variety. The spikelet length is approximately 2.4 mm and spikelet width is approximately 0.9 mm. The number of spikelets per ear is 14.

Spring vigor is good and fall vigor is moderate compared to the comparative test varieties. Tolerance to summer blight is on par with 'Meyer' and 'Emerald', and slightly improved for wintering ability. The leaves are rolled in a bud shoot. The leaf width is very fine, around 1.3 mm, and the leaf length is around 12.6 mm.

The leaf color in 'NARUO1920' is a deeper green than the control variety 'Emerald' and slightly lighter green than 'Meyer'. The leaf blade is flat, with a round bottom, and gradually tapers to an acute point. Mature leaf blades have some trichomes on the front side and few on the underside. The leaf sheath is hairless.

The typical height of 'NARUO1920' is 3.2 cm; that of 'TM9' is 5.8 cm; that of 'Meyer' is 9.6 cm and that of 'Emerald' is 4.8 cm.

The typical spread per 100 $cm^2$ of 'NARUO1920' is 344 $cm^2$; that of 'TM9' is 288 $cm^2$; that of 'Meyer' is 125 $cm^4$ and that of 'Emerald' is 175 $cm^2$. Spread value is defined as the length of the stolon per unit area.

The typical culm length of 'NARUO1920' is 3.1 cm; that of 'TM9' is 4.4 cm; that of 'Meyer' is 7.0 cm that of 'Emerald' is 4.8 cm.

The typical culm width of 'NARUO1920' is 1.0 mm; that of 'TM9' is 1.5 mm; that of 'Meyer' is 2.5 mm that of 'Emerald' is 2.2 mm.

The typical culm color of 'NARUO1920' is 140B; that of 'TM9' is 60A; that of 'Meyer' is 60A that of 'Emerald' is 60A based on The R.H.S. Color Chart.

The flag leaf width of 'NARUO1920' is 0.43 mm; that of 'TM9' is 0.8 mm; that of 'Meyer' is 0.8 mm that of 'Emerald' is 0.7 mm.

The typical inflorescence length of 'NARUO1920' is 8.5 mm; that of 'TM9' is 26 mm; that of 'Meyer' is 34 mm that of 'Emerald' is 30 mm.

The typical inflorescence width of 'NARUO1920' is 0.59 mm; that of 'TM9' is 1.0 mm; that of 'Meyer' is 1.5 mm that of 'Emerald' is 1.0 mm.

The typical color of spikelets (matured) of 'NARUO1920' is 158B; that of 'TM9' is 158D; that of 'Meyer' is 158A that of 'Emerald' is 158B.

The typical length of spikelets of 'NARUO1920' is 2.4 mm; that of 'TM9' is 2.6 mm; that of 'Meyer' is 3.2 mm that of 'Emerald' is 2.9 mm.

The number of spikelets of 'NARUO1920' is 14; that of 'TM9' is 22; that of 'Meyer' is 30, and that of 'Emerald' is 19 mm.

The flowering period of 'NARUO1920' comprises October 18; that of 'TM9' is April 22; that of 'Meyer' comprises March 6 that of 'Emerald' comprises March 23 as measured at Kawanishi, Hyogo, Japan.

Other Descriptive Values

Leaf blade length. The typical leaf blade length of 'NARUO1920' is 12.6 mm; that of 'TM9' is 37.5 mm; that of 'Meyer' is 95.0 mm, and that of 'Emerald' is 56.5 mm.

Leaf blade width. The typical leaf blade width of 'NARUO1920' is 1.1 mm; that of 'TM9' is 1.8 mm; that of 'Meyer' is 3.7 mm, and that of 'Emerald' is 1.8 mm.

Leaf blade intensity of green color. The typical leaf blade intensity of green color of 'NARUO1920' is 140B; that of 'TM9' is 142C; that of 'Meyer' is 141C, and that of 'Emerald' is 142C.

Leaf blade margin. The leaf blade margin of 'NARUO1920' is smooth; that of 'TM9' is smooth, that of 'Meyer' is smooth, and that of 'Emerald' is smooth.

The leaf blade density of hairs of 'NARUO1920' is very sparse (about ≤1 hair/leaf); that of 'TM9' is very sparse, that of 'Meyer' is sparse (≥1 hair/leaf) and that of 'Emerald' is sparse.

As described above a 'NARUO1920' plant may be asexually reproduced by cutting it into 2-3 stems in April at Kawanishi, Hyogo, Japan and transplanting them one by one into a polyethylene pot (φ60 mm) filled with culture soil (bed soil) and grown for about one month.

FIGS. 6A-6D summarize the comparison of leaf length, ear emergence stem length, number of ears, and stolon density, which are characteristic of 'NARUO1920'. 'NARUO1920' had much lower values of above-ground traits (leaf length and ear emergence stem length) compared to the control and standard varieties, while the stolon density was the highest, therefore, it was found to be a small plant with excellent stolon growth. The results are consistent with the results in 2019. The number of ears was extremely high, but since the golf course is mowed frequently and ears are cut regularly, the number of ears is not considered to be a problem. These results were obtained from a variety registration test which compared 'NARUO1920' to 'TM9', 'Emerald' and 'Meyer' plants. In the nursery at the university, each cultivar was cut into 2-3 stems in April 2021 and transplanted one by one into a polyethylene pot (φ60 mm) filled with culture soil (bed soil) and grown for about one month. The method of cultivation and research was conducted in accordance with the Criteria and Characteristics Table (*Zoysia* Wild) on the registration website on: the world wide web <hinshu2.maff.go.jp/info/sinsakijun/kijun/1670.pdf>. Additional traits were assessed using the 25 parameters listed in Table 1 which follows.

TABLE 1

Phenotype and characteristics of 'NARUO1920'

| Plant characteristics | State | Value |
|---|---|---|
| Plant habit | prostrate | |
| Stem size | large | 1.3 mm |
| Stem length | very short | 14.9 mm |
| Stolon density | very long | 344 cm |
| Leaf length | very short | 12.6 mm |
| Leaf width | narrow | 1.3 mm |
| Leaf Color | medium | |
| Ear length | very short | 8.5 mm |
| Ear color | medium | |
| Spike let length | a little short | 2.4 mm |
| Spike let width | medium | 0.9 mm |
| Number of spikelet per ear | few | 14 |
| Attachment of husk | semi-husked | |
| Vigor of early stage | a little good | |
| Spring vigor | a little poor | |
| Fall vigor | medium | |
| Head emergence | a little early | Oct 24 |
| Heading in spring and/or Fall | only Fall | |
| Number of ear | very many | |
| Regrowth vigor | poor | |
| Greening time | a little late | |
| Coloring time | medium | |
| Wintering ability | a little good | |
| Tolerance to summer depression | good | |

The invention claimed is:

1. A new and distinct variety of *Zoysia* grass plant named 'NARUO1920' as illustrated and described herein particularly characterized by a unique combination of morphological features.

* * * * *

'NARUO1920'

'Mayer'

'Emerald'

'NARUO1920'

'Mayer'

'Emerald'

FIG. 4A compares the greenness of the experimental plots from 2022.05 to 2023.05.
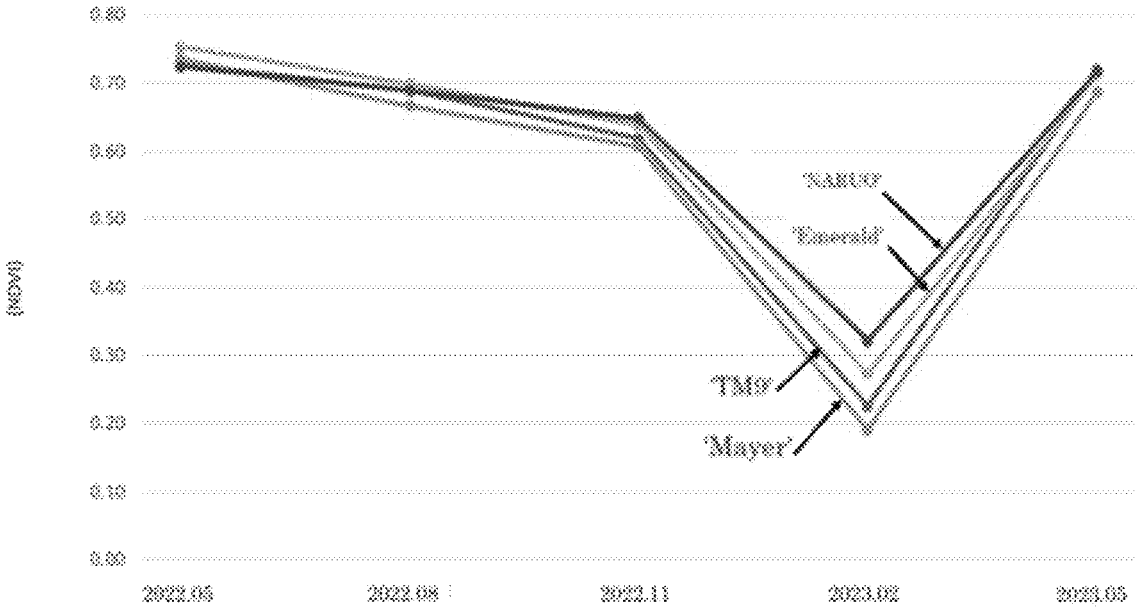
| | 2022.05 | 2022.08 | 2022.11 | 2023.02 | 2023.05 |
|---|---|---|---|---|---|
| 'TM9' | 0.73 | 0.68 | 0.62 | 0.33 | 0.72 |
| 'Mayer' | 0.74 | 0.67 | 0.61 | 0.39 | 0.69 |
| 'Emerald' | 0.75 | 0.70 | 0.64 | 0.37 | 0.73 |
| 'NARUO' | 0.72 | 0.69 | 0.65 | 0.32 | 0.72 |
FIG. 4B shows the increased greenness of the NARUO1920 plot compared to the plots of TM9, Mayer, and Emerald varieties.
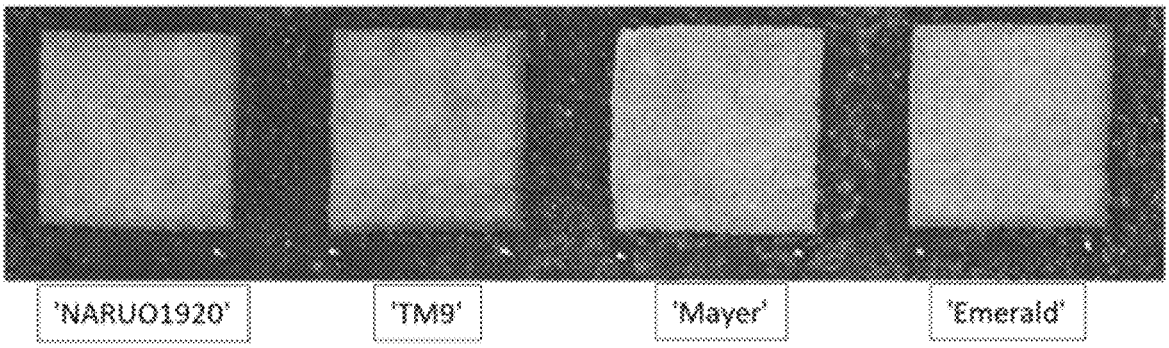

Figures 1, 5B:
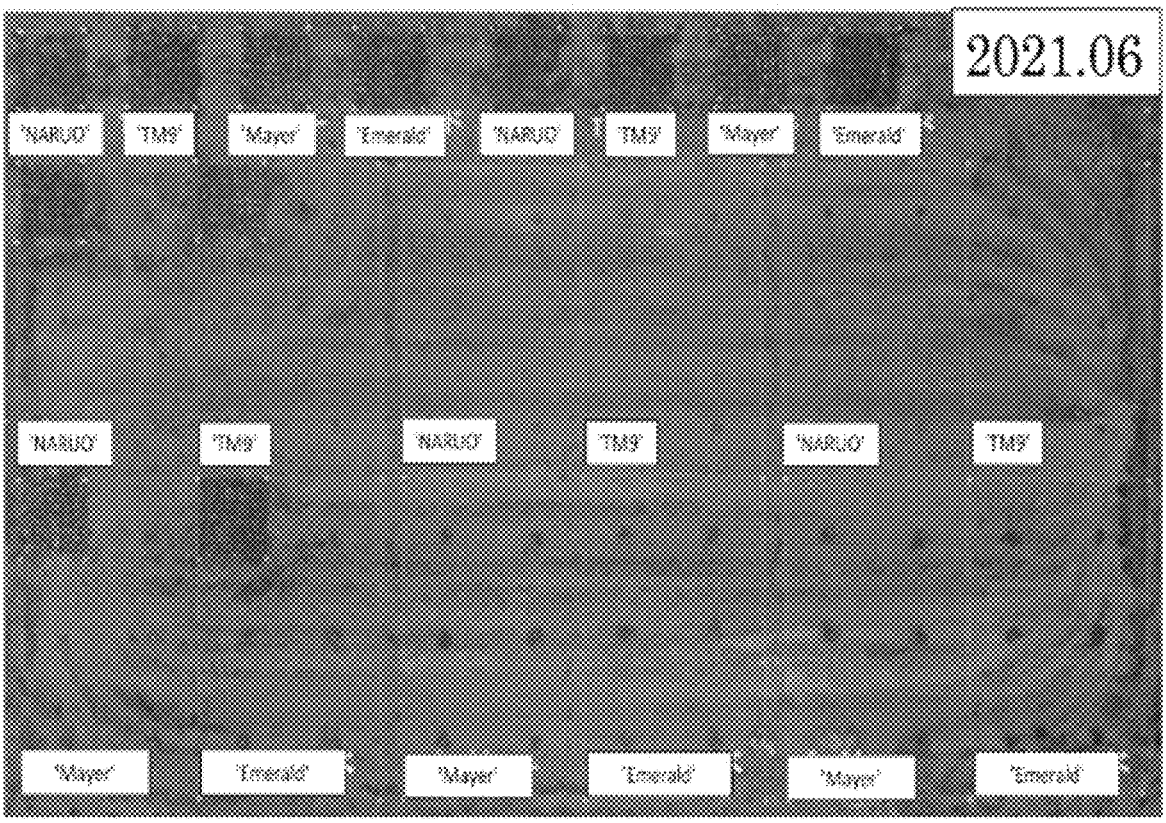
Figures 2, 5B:
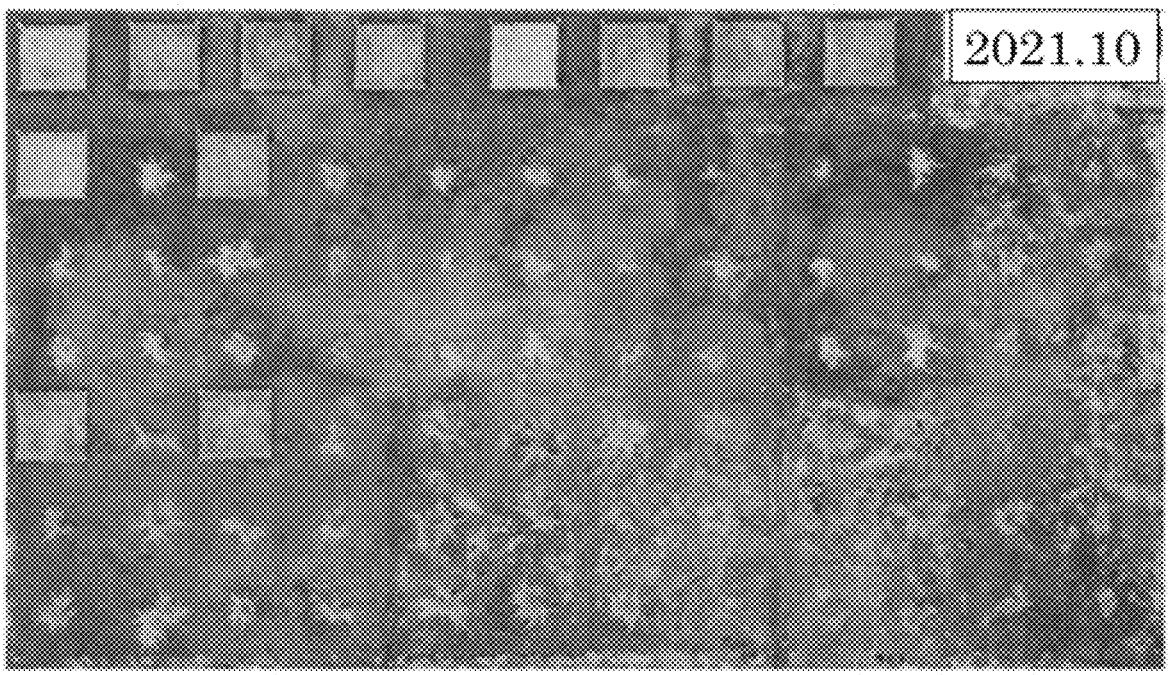
Figures 3, 5B:
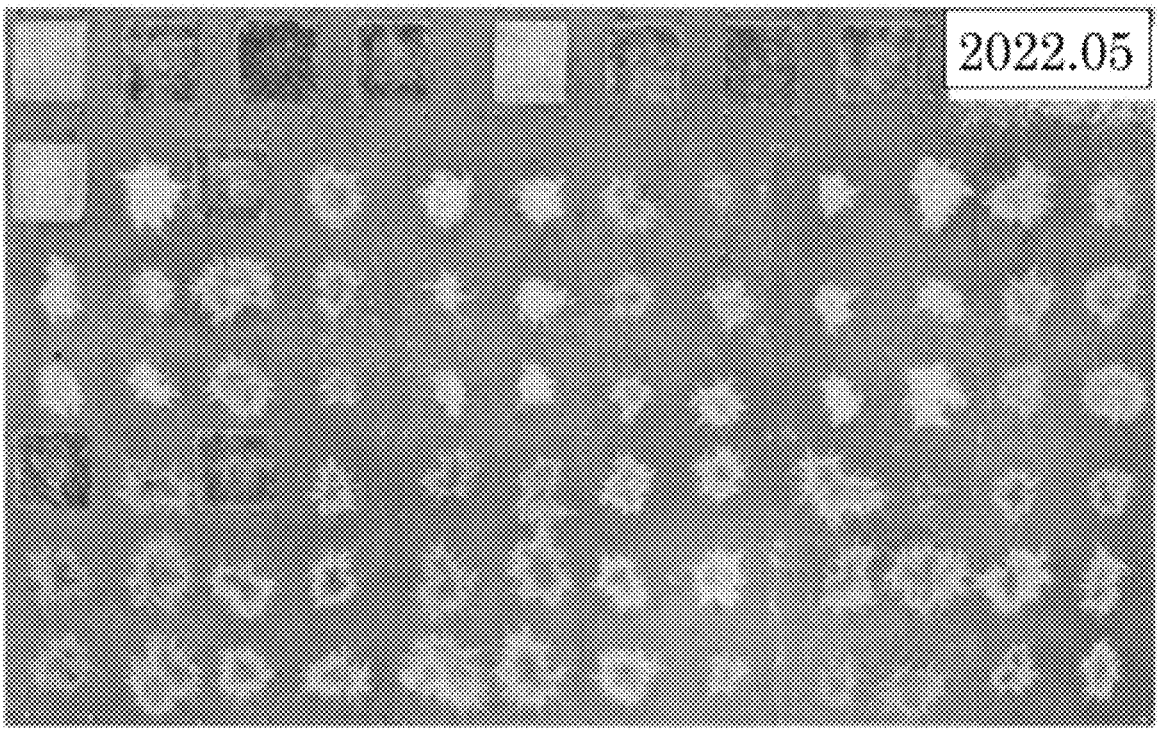
Figures 4, 5B:
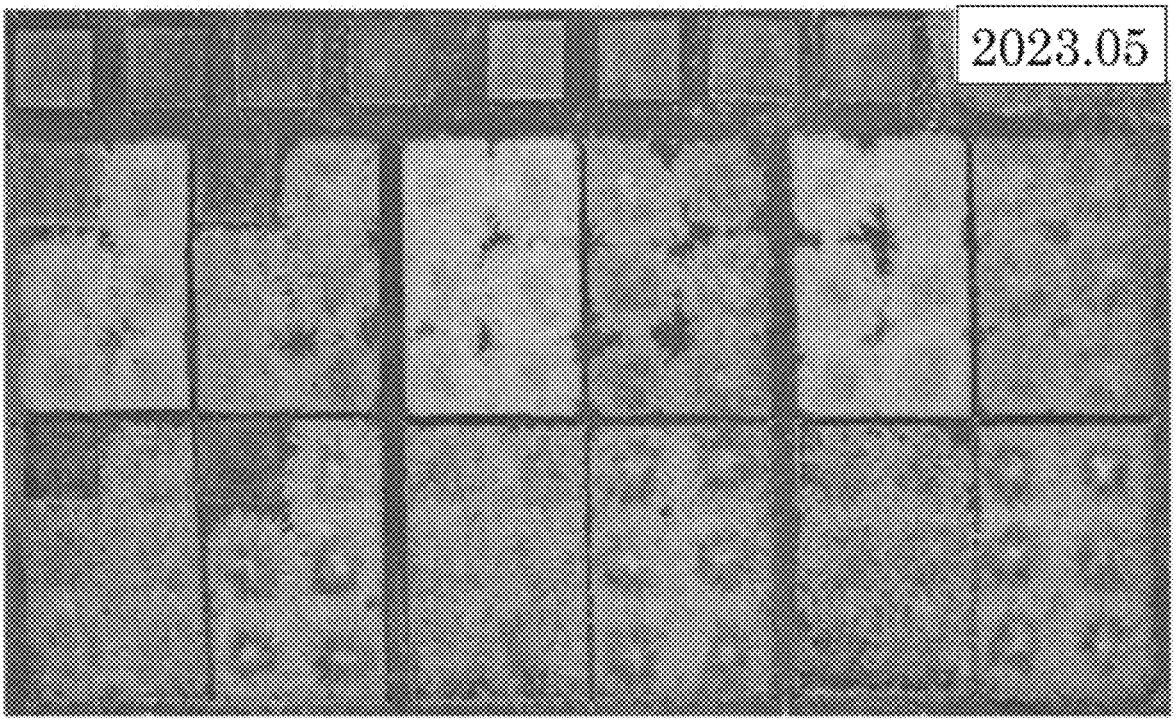

FIG. 5A shows initial growth in June, July and August for NARUO1920, TM9, Mayer, and Emerald varieties.
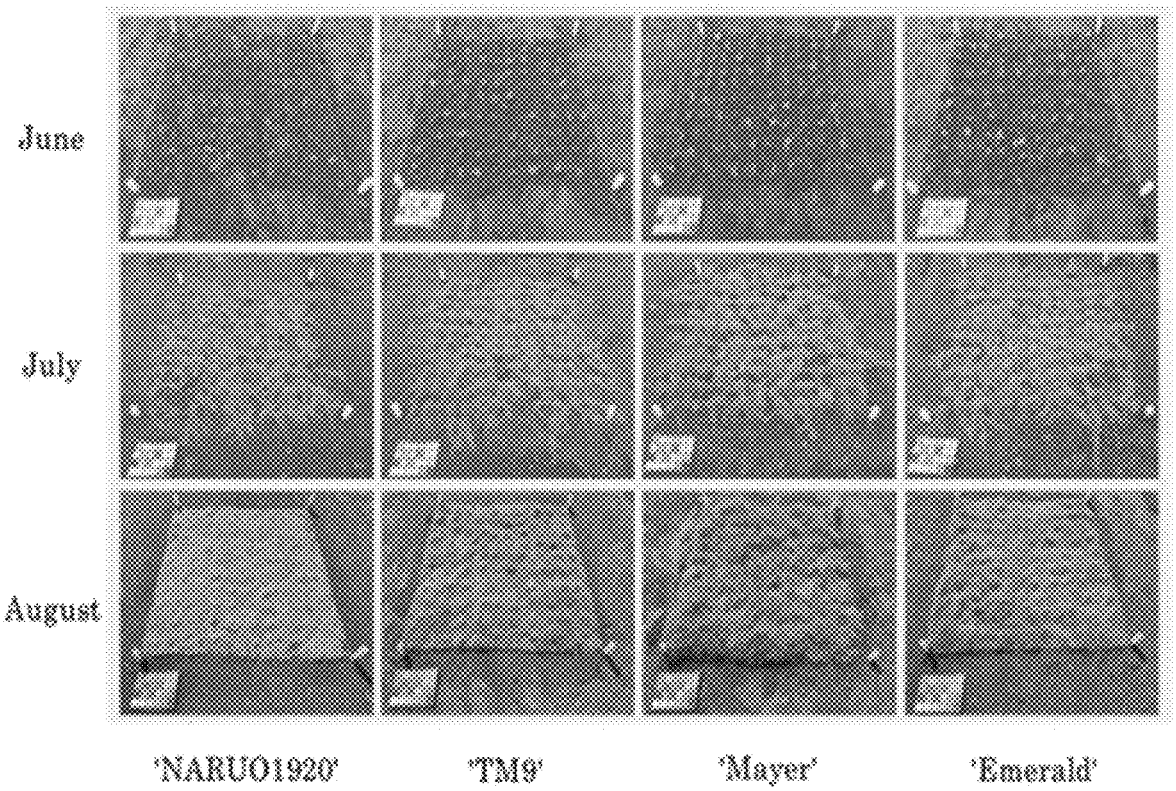

FIG. 6A. Bar graphs comparing leaf length. The first bar is NARUO1920 and the second to fourth bars are, respectively, the TM9, Mayer, and Emerald varieties.
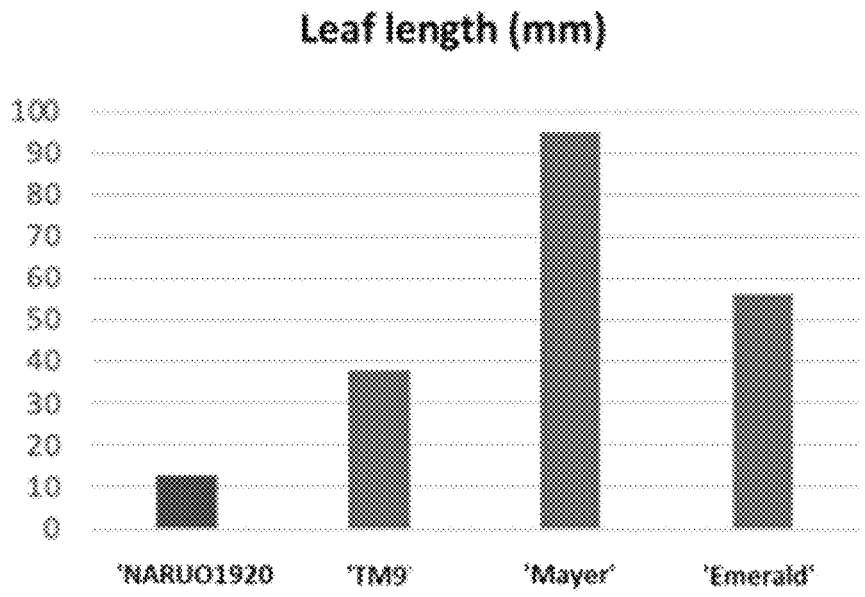
FIG. 6B. Bar graphs comparing stem length. The first bar is NARUO1920 and the second to fourth bars are, respectively, the TM9, Mayer, and Emerald varieties.
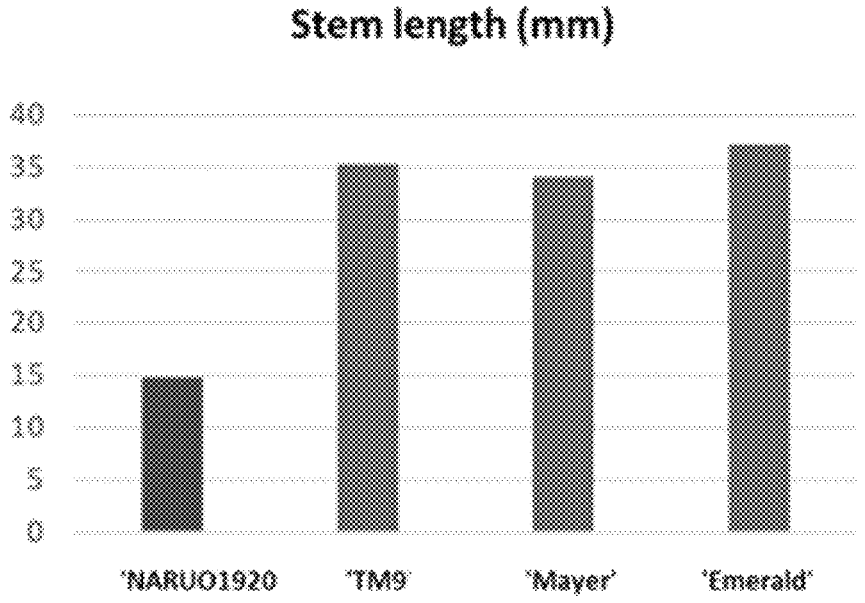

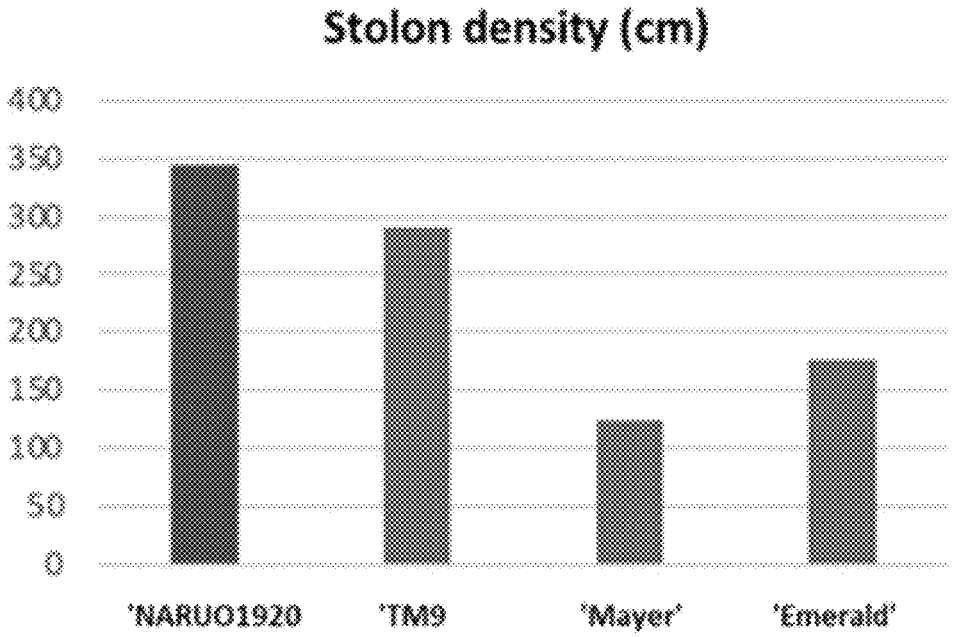

FIG. 6C. Bar graphs comparing number or ears in Fall (Japan). The first bar is NARUO1920 and the second to fourth bars are, respectively, the TM9, Mayer, and Emerald varieties.
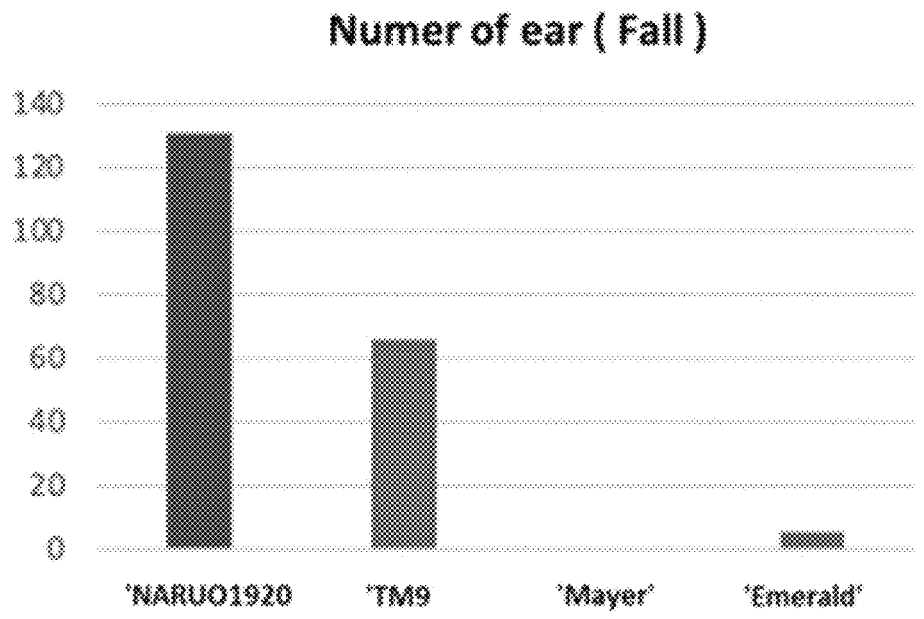
FIG. 6D. Bar graphs comparing stolon density (cm). The first bar is NARUO1920 and the second to fourth bars are, respectively, the TM9, Mayer, and Emerald varieties.